Figure 1:
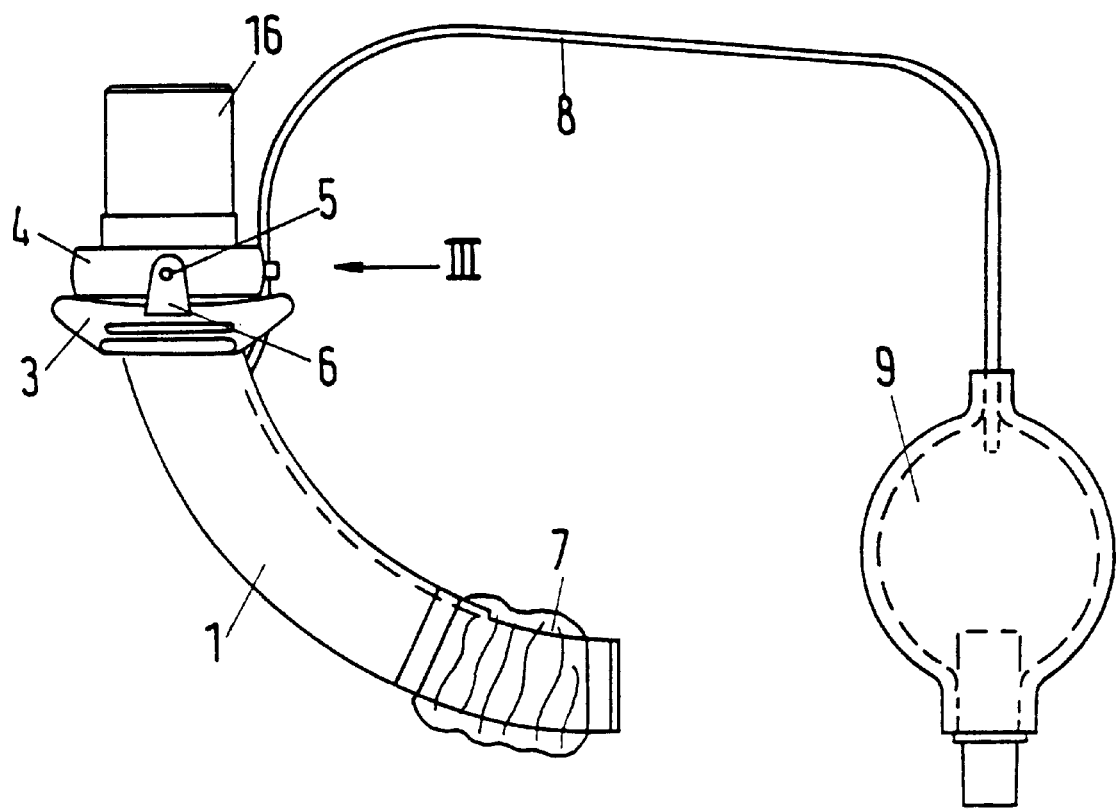

United States Patent [19]
Waldeck

[11] Patent Number: 6,053,167
[45] Date of Patent: Apr. 25, 2000

[54] TRACHEOSTOMY CANNULA

[75] Inventor: Franz Waldeck, Deutschland, Germany

[73] Assignee: Tracoe Gesellschaft fü medizinische, Neu-Isenburg, Germany

[21] Appl. No.: 08/930,658

[22] PCT Filed: Apr. 13, 1996

[86] PCT No.: PCT/DE96/00688

§ 371 Date: Oct. 1, 1997

§ 102(e) Date: Oct. 1, 1997

[87] PCT Pub. No.: WO96/33760

PCT Pub. Date: Oct. 31, 1996

[30] Foreign Application Priority Data

Apr. 24, 1995 [DE] Germany .................. 195 14 433

[51] Int. Cl.[7] ................................................. A61M 16/00
[52] U.S. Cl. .................. 128/207.14; 128/207.17; 128/200.26; 128/912; 623/9
[58] Field of Search .................. 128/207.14, 207.15, 128/200.26, 207.17, DIG. 26, 207.16, 912; 604/58; 623/9

[56] References Cited

U.S. PATENT DOCUMENTS

| | | |
|---|---|---|
| 3,236,236 | 2/1966 | Hudson . |
| 3,659,612 | 5/1972 | Shiley et al. ................. 128/351 |
| 3,824,999 | 7/1974 | King . |
| 3,987,798 | 10/1976 | McGinnis ................. 128/DIG. 26 |
| 4,009,720 | 3/1977 | Crandall ................. 128/351 |
| 4,033,353 | 7/1977 | La Rosa ................. 128/351 |
| 4,235,229 | 11/1980 | Ranford et al. ................. 128/207.17 |
| 4,304,228 | 12/1981 | Depel ................. 128/200.26 |
| 4,686,977 | 8/1987 | Cosma ................. 128/207.17 |
| 4,852,565 | 8/1989 | Eisele ................. 128/207.14 |
| 5,054,482 | 10/1991 | Bales ................. 128/912 |
| 5,056,515 | 10/1991 | Abel ................. 128/200.26 |
| 5,067,496 | 11/1991 | Eisele ................. 128/207.15 |
| 5,361,754 | 11/1994 | Stuart ................. 128/207.17 |
| 5,458,139 | 10/1995 | Pearl ................. 128/207.14 |

FOREIGN PATENT DOCUMENTS

| | | | |
|---|---|---|---|
| 0037719 | 7/1985 | European Pat. Off. . | |
| 0107779 | 12/1986 | European Pat. Off. . | |
| 0598948 | 6/1994 | European Pat. Off. ................. | 16/4 |
| 3819237 | 12/1988 | Germany ................. | 16/4 |
| 2007789 | 5/1979 | United Kingdom ................. | 27/4 |
| 2205504 | 12/1988 | United Kingdom . | |

*Primary Examiner*—John G. Weiss
*Assistant Examiner*—V. Srivastava
*Attorney, Agent, or Firm*—Biebel & French

[57] ABSTRACT

A tracheostomy cannula for use in a tracheostoma is described, which is provided with a hose-like outer cannula into which an inner cannula, which is also hose-like, can be guided and can be locked to the outer cannula at the proximal part in order to form a cannula tube, wherein a cannula plate (3) for application to the neck is fitted in the proximal area of the outer cannula (1), through which the proximal part of the outer cannula reaches (1). It is proposed that the cannula tube is mounted so that it is pivotable about at least two spatial axes (X, Y) with respect to the cannula plate (3).

4 Claims, 4 Drawing Sheets

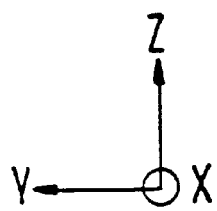
Fig.6
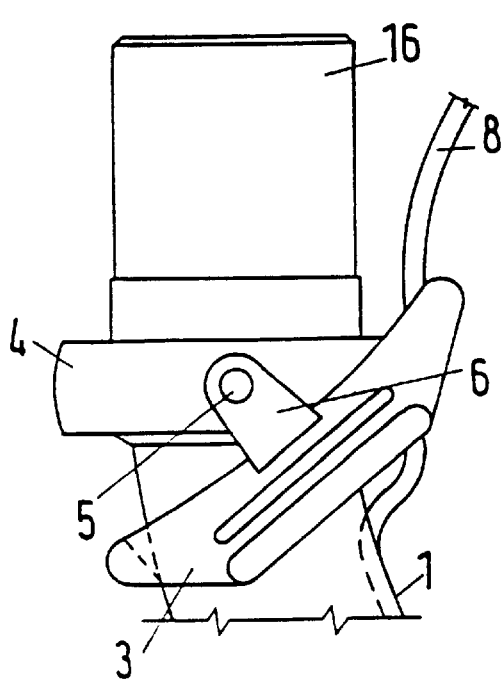
Fig.7
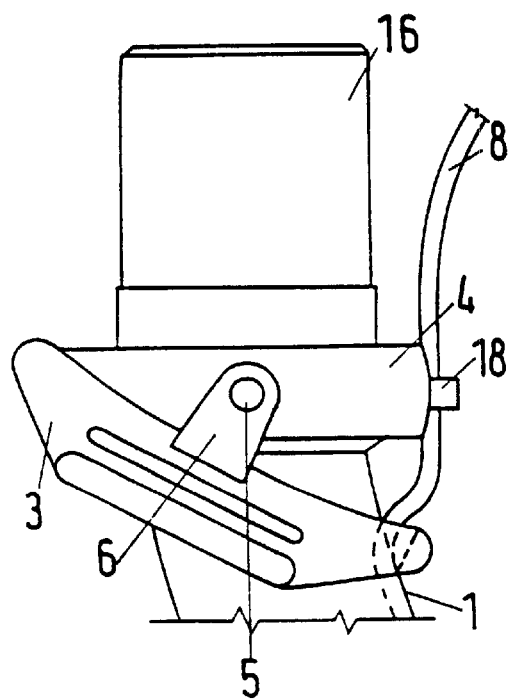

TRACHEOSTOMY CANNULA

The invention relates to a tracheostomy cannula for insertion in a tracheostoma, in accordance with the preamble of claim 1. It is provided with a hose-like outer cannula, inside which an inner cannula, which is also hose-like, can be guided and locked to the proximal part of the outer cannula, whereby in the proximal area of the outer cannula, a cannula plate for placing on the neck of the patient is fitted. The outer cannula and inner cannula together form the cannula tube.

Tracheostomy cannulas of this type with a cannula plate pivotable about one axis only have been long known. Reference is made in this connection to U.S. Pat. No. 5,067,496, EP-0 107 779 B1, EP-0 037 719 B1, U.S. Pat. No. 4,852,565 and U.S. Pat. No. 4,009,720 in the patent literature.

Tracheostomy cannulas of this type are inserted in a tracheostoma resulting from an operation, in order to keep it open until it heals. There are circumstances, however, in which a tracheostomy cannula must remain permanently in the tracheostoma. In other cases, the tracheostomy cannula assists artificial respiration.

The outer cannula can be inserted in the trachea, widening the tracheostoma with the aid of a so-called guide rod (stylet or obturator). The outer cannula keeps the tracheostoma open and needs only to be removed from time to time for cleaning. On the proximal side of the outer cannula there is fitted a so-called cannula plate, which lies against the patient's neck when the tracheostomy cannula is in the tracheostoma. The cannula plate prevents, inter alia, the tracheostomy cannula from being inserted too far into the trachea or from sliding down into it.

The correspondingly configured hose-like inner cannula fits exactly inside the outer cannula, and can be easily removed from it for frequent cleaning. This has the advantage that the outer cannula does not also have to be removed from the trachea and the tracheostoma, which could otherwise result in pain and injuries.

The tracheostomy cannulas known from the documents listed above have a cannula plate with respect to which the cannula tube is mounted pivotally about one axis, that is to say about the horizontal axis. For this purpose, the cannula plate is provided with an aperture through which the outer cannula reaches. Two pegs project into the aperture, which engage with corresponding holding means in the external area of the outer cannula such that the cannula tube is pivotable in a certain range of approximately ±45° with respect to the cannula plate. A degree of wearer comfort is produced by means of this pivoting, to the extent that when the patient bends or lifts his or her head, the tracheostomy cannula can adjust its position to a certain degree so that the pain which a patient feels when, for example, the cannula is pressed against the front or rear wall of the trachea, is reduced.

Nevertheless, the resulting wearer comfort of the known tracheostomy cannulas is not yet satisfactory.

A tracheostomy cannula of the type described in the preamble is known from U.S. Pat. No. 4,686,977. In this a tracheostomy cannula is described wherein the cannula plate is mounted by means of a ball joint in the proximal part of the cannula. This type of mounting allows the pivoting of the cannula tube with respect to the cannula about the three spatial axes X, Y and Z. This proposal provided a theoretical approach as to how the wearer comfort of such a tracheostomy cannula could be improved. However, the production of this tracheostomy cannula ran into difficulties. There is, on the one hand, insufficient pivoting of the cannula tube with respect to the cannula plate, as the outer half-shell jaw has to enclose the ball in the joint to a comparatively large degree in the interests of safety, as otherwise there is the danger of the cannula becoming detached from the mounting and falling into the trachea. On the other hand, the fixing of the inner cannula is difficult to effect, in particular having regard to the replacement of the inner cannula which has to be done very frequently. The document described does not offer any proposals for solutions to the fixing of the inner cannula. The known types of fixing were therefore conceivable, such as by means of a bayonet fitting. However, if the connection were made using a bayonet fitting, there would be a movement about the third spatial axis Z. This rotation is dangerous to the patient, however, both when awake and when sedated, for example, as without additional measures the cannula tube presses too hard laterally against the trachea wall.

Given this background, the object of the present invention is to further develop a tracheostomy cannula of the type described in the preamble such that a sufficient degree of pivoting about two spatial axes is possible, and the pivoting is produced in relatively simple technical manner.

This object is solved according to the invention by means of the tracheostomy cannula with the features of the characterising part of claim 1. Further advantageous embodiments result from the dependent claims.

It is firstly provided that the ability to pivot about the spatial Y axis is produced by means of a ring gripping around the outer cannula and rotatably mounted thereupon, and the ability to pivot about the spatial X axis is provided by means of rotatable mounting of the cannula plate on the ring. If the cannula plate is ideally considered as a ring, the invention is effected in that two rings rotatable with respect to one another, that is to say the inner ring with respect to the outer ring (cannula plate), are pivotally mounted on the outer cannula. This implementation is relatively simple in terms of construction, but very effective and inexpensive.

The rotatable mounting, in the previously described case, of the ring on the outer cannula and of the cannula plate on the ring, is preferably provided by pegs, which can be configured in correspondingly configured recesses in the canula, the ring and the cannula plate. This depends on where the pegs are arranged.

The dimensions in the case previously described are preferably selected such that the cannula tube is pivotable with respect to the cannula plate about the Y axis by ±25° and about the X axis by ±60°.

Figure 2:
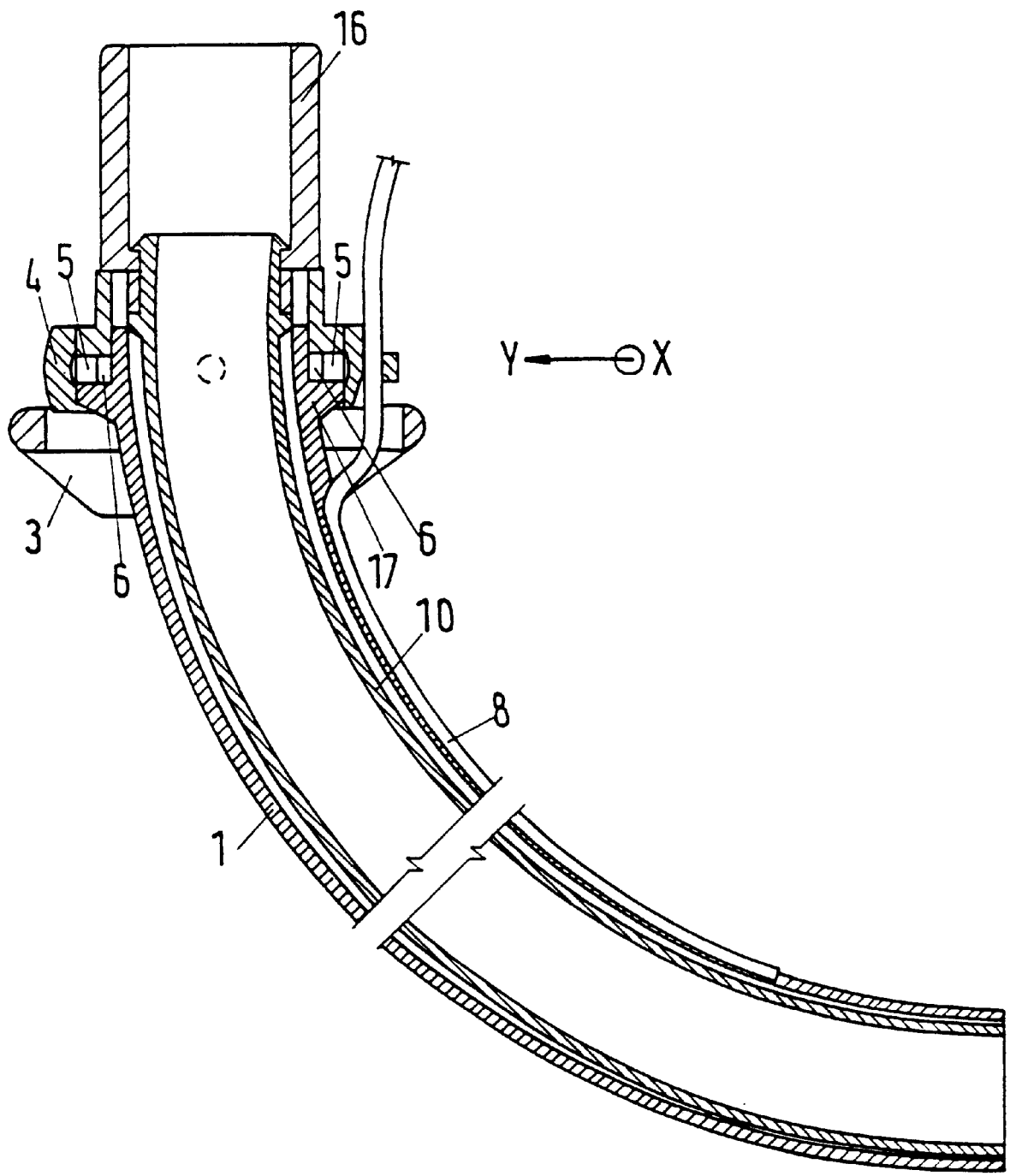
Figure 3:
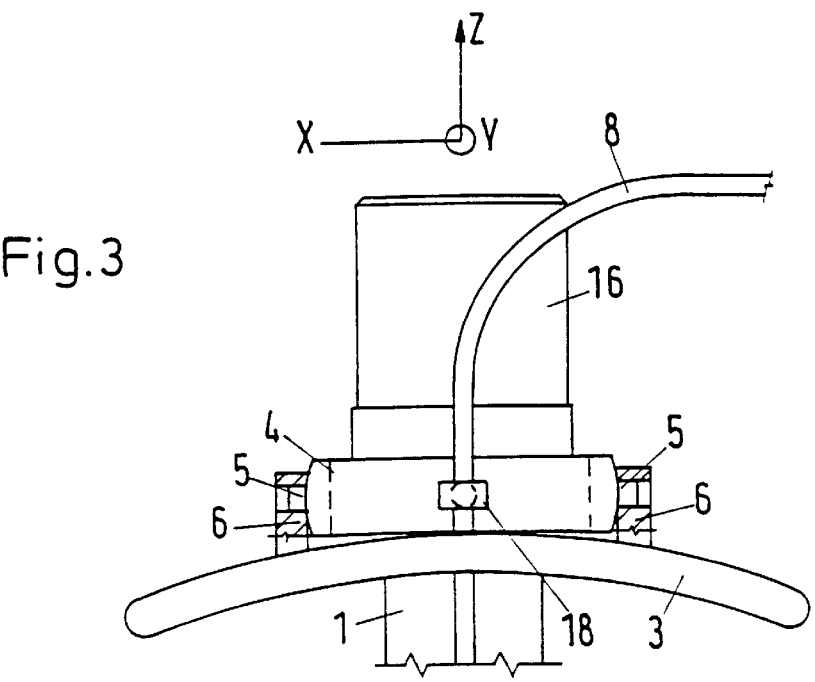
Figure 4:
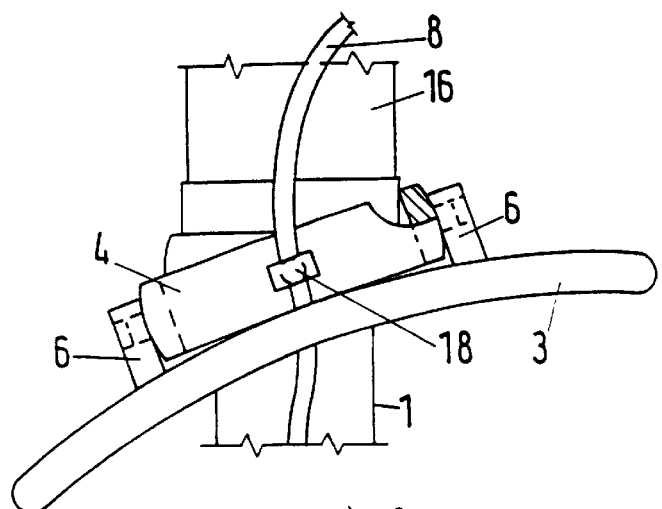
Figure 5:
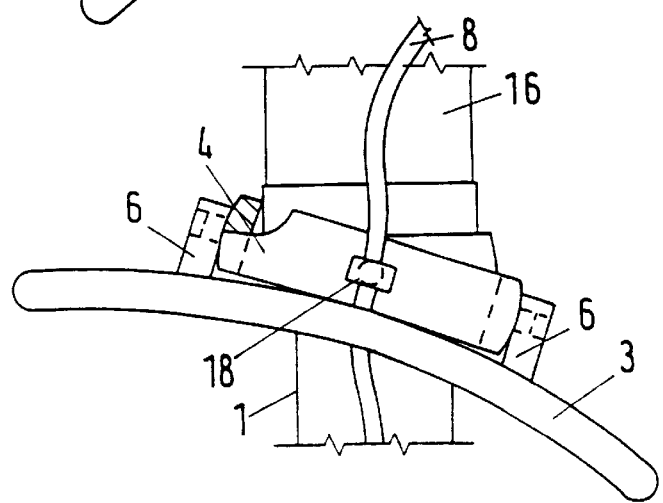

The invention will hereinafter be described in more detail with the aid of an embodiment with reference to the drawings. In these is shown, in:

FIG. 1 a view of the tracheostomy cannula with a cuff and control balloon,

FIG. 2 a sectional view through the tracheostomy cannula according to FIG. 1,

FIG. 3 a detail view in the direction of the arrow III in FIG. 1,

FIG. 4 a similar view as in FIG. 3, however with a cannula plate pivoted to one side, FIG. 5 a similar view as in FIG. 4, with the cannula plate pivoted to the other side, FIG. 6 a detail view of the proximal area of the tracheostomy cannula according to FIG. 1 with a cannula plate pivoted in one direction about the X-axis, and FIG. 7 a similar view as in FIG. 6 with a cannula plate pivoted to the other side.

Hereinafter, like parts have like designations.

FIG. 1 gives the first rough overview of the tracheostomy cannula according to the invention. It is composed of an outer cannula 1, into which an inner cannula (not shown in FIG. 1) is guided. A connecting part 16 in accordance with DIN ISO 5356-1 (1987) which projects from the patient's tracheostoma is moulded onto the inner cannula. When the tracheostomy cannula has been completely inserted through the tracheostoma into the trachea, the cannula plate 3, which is fitted to the proximal area of the outer cannula 1, lies against the patient's neck.

The cannula tube, composed of the outer cannula and the inner cannula, is arranged such that it can pivot about two spatial axes with respect to the cannula plate (3) by means of the parts labelled with the designations 4, 5 and 6, as will be explained later in more detail.

Lying at the front in the distal area of the outer cannula 1, there is arranged a balloon or cuff 7 which can be inflated by means of an air line 8 outside the body, so that the distal end of the tracheostomy cannula can be brought into a defined position with respect to the wall of the trachea and so that a seal between the outer cannula and air tube can be produced. This is done by inflating the balloon or cuff 7 from the exterior and is controlled by the control balloon 9.

Details of the constructional design of the tracheostomy cannula can be seen from FIG. 2, which shows a sectional view. Here, it is clearly evident how the inner cannula 10 is guided into the outer cannula 1. The ability of the canula plate 3 to pivot about the axis, shown in the drawing as horizontal (Y axis) is here produced in that a ring 4 grips the outer cannula 1 in the proximal area and is rotatably mounted upon it by means of the peg 5 projecting into the inside of the ring, which engage with cut-outs or recesses 6 in a shoulder 17 moulded onto the proximal end of the outer cannula 1. To make the ability to pivot about the axis (X axis) perpendicular to the plane of the drawing possible, the cannula plate 3 is mounted in a rotatable manner, connected to the ring 4. This can, however, be more clearly seen in FIGS. 3 to 5. As clearly illustrated in FIG. 2, the X and Y axes are disposed substantially parallel to the cannula plate 3 and the X a is disposed perpendicular to the Y axis.

FIG. 3 shows the enlarged partial view, in the direction of the arrow III in FIG. 1, of the proximal area of the tracheostomy cannula. At the top is the system of coordinates to which details of the spatial axes relate.

FIG. 3 firstly shows the rotatable mounting of the cannula plate 3 on the ring 4. From the ring there project two pegs 5 which engage with two cut-outs or eyelets 6 which are moulded in the cannula plate 3. The ability to pivot about the X axis in the system of coordinates set out is obtained in this way.

FIG. 3 again shows the connecting piece 16 and the outer cannula 1. The hose 8 which leads to the balloon 7 (FIG. 1) is also shown, and how it is fixed through and into a retaining eyelet 18 onto the ring 4.

FIGS. 4 and 5 very clearly show the possibilities for pivoting about the Y axis which is made possible by the mounting which was described with reference to FIG. 2.

FIGS. 6 and 7 show the view of the proximal area of the tracheostomy cannula displaced by 90° with respect to FIGS. 3 to 5, that is to say seen from the right. The ability of the cannula plate 3 to pivot about the X axis is clearly shown. The details of the mounting were described with reference to FIG. 3.

I claim:

1. Trachcostomy cannula for use in a tracheostoma, said cannula comprising:

a tubular outer cannula (1) having a proximal part and a distal part;

a tubular inner cannula (10) guided and locked within the outer cannula (1) at the proximal part in order to form a cannula tube having a tube axis;

a cannula plate (3) for attachment to a patient's neck, the cannula plate (3) receiving the proximal part of the outer cannula of the cannula tube, the cannula tube mounted such that it is able to pivot about X and Y spatial axes with respect to the cannula plate (3), the X and Y axes disposed substantially parallel to the cannula plate (3) and substantially perpendicular to the tube axis, the X axis disposed perpendicular to the Y axis and the canula tube supported for pivotal movement about the Y axis;

means for pivoting the cannula tube about the Y axis obtained by a ring (4) gripping around the outer cannula (1), the ring (4) pivotally mounted on the outer cannula for pivotal movement of the X axis relative to the tube axis; and means for pivoting the canoula tube about the X axis obtained by pivotal mounting of the cannula plate (3) on the ring (4).

2. Tracheostomy cannula according to claim 1, characterised in that the range of pivoting about the Y axis is ±25° and about the X axis is ±60°.

3. Tracheostomy cannula according to claim 1, characterised in that the pivotal mounting of the ring (4) on the outer cannula (1) and of the cannula plate (3) on the ring (4) is effected by pegs (5) which engage with correspondingly configured cut-outs (6).

4. Tracheostomy cannula according to claim 2, characterised in that the pivotal mounting of the ring (4) on the outer cannula (1) and of the cannula plate (3) on the ring (4) is effected by pegs (5) which engage with correspondingly configured cut-outs (6).

* * * * *